United States Patent [19]

Hayden et al.

[11] 4,007,135

[45] Feb. 8, 1977

[54] PROMOTED SILVER CATALYST FOR PRODUCING ALKYLENE OXIDES

[75] Inventors: Percy Hayden; Roy John Sampson; Christopher Buxton Spencer; Harry Pinnegar, all of Billingham, England

[73] Assignee: Imperial Chemical Industries Limited, London, England

[22] Filed: Nov. 22, 1974

[21] Appl. No.: 526,431

[30] Foreign Application Priority Data

| | | |
|---|---|---|
| May 12, 1973 | United Kingdom | 56369/73 |
| Sept. 1, 1974 | United Kingdom | 974/74 |
| Sept. 1, 1974 | United Kingdom | 972/74 |
| Mar. 4, 1974 | United Kingdom | 14786/74 |
| Mar. 4, 1974 | United Kingdom | 14787/74 |
| May 24, 1974 | United Kingdom | 23276/74 |
| May 24, 1974 | United Kingdom | 23278/74 |
| May 30, 1974 | United Kingdom | 24071/74 |
| May 30, 1974 | United Kingdom | 24072/74 |
| Aug. 5, 1974 | United Kingdom | 34333/74 |
| Aug. 19, 1974 | United Kingdom | 36357/74 |
| Sept. 19, 1974 | United Kingdom | 40882/74 |

[52] U.S. Cl. ............................ 252/467; 252/475; 252/476; 260/348.5 R

[51] Int. Cl.$^2$ .................... B01J 23/50; B01J 23/68

[58] Field of Search .......... 252/463, 476, 467, 475; 260/348.5 R

[56] References Cited

UNITED STATES PATENTS

| | | | |
|---|---|---|---|
| 2,040,782 | 5/1936 | Van Peski | 252/476 X |
| 2,404,438 | 7/1946 | Evans | 252/476 X |
| 2,799,687 | 7/1957 | Gould et al. | 252/476 X |
| 2,831,870 | 4/1958 | McClements et al. | 252/476 X |
| 3,144,416 | 8/1964 | Hosoda et al. | 252/476 |
| 3,563,914 | 2/1971 | Wattimena | 252/463 |
| 3,664,970 | 5/1972 | DeMaio | 252/476 X |
| 3,725,307 | 4/1973 | Brown et al. | 252/476 X |

*Primary Examiner*—W. J. Shine
*Attorney, Agent, or Firm*—Cushman, Darby & Cushman

[57] ABSTRACT

Alkylene oxides are produced by oxidizing olefines with oxygen in the presence of promoted silver containing catalysts.

6 Claims, No Drawings

PROMOTED SILVER CATALYST FOR PRODUCING ALKYLENE OXIDES

This invention relates to the production of alkylene oxides and catalysts therefor.

Ethylene oxide is normally produced by the catalytic oxidation of ethylene with oxygen (which may be supplied in the form of air). Part of the ethylene is oxidised to oxides of carbon and water, and it is desirable that the proportion of ethylene consumed in this way should be as small as possible; that is, that the reaction should be as selective as possible in forming the desired product, namely ethylene oxide. Catalysts should, therefore, be employed which make this possible, but they should be sufficiently active to make an acceptable rate of production possible. Thus, an important feature of a catalyst is that it should show a good combination of activity and selectivity under its intended reaction conditions.

This invention provides catalysts for the production of alkylene oxides, for example ethylene and propylene oxides, by oxidation of the corresponding olefin with oxygen, which comprise silver supported on and introduced by impregnation with an alkaline solution of a decomposable silver compound to a preformed porous heat resisting support which has a specific surface area in the range 0.04 to 10 $m^2/g$ preferably 0.05 to 3 $m^2/g$, more preferably 0.1 to 1.5 $m^2/g$, and especially 0.2 to 0.6 $m^2/g$ as measured by the Brunauer, Emmett and Teller method, an apparent porosity as measured by the mercury absorption method of at least 20%, perferably 30 to 65%, and more preferably 40 to 60%, for example 45 to 55% and median pore diamters of 0.3 to 15 microns, preferably 1 to 15 microns as measured by the mercury porosimetry method, the catalyst also comprising a promoting amount of copper, gold, zinc, cadmium, mercury, niobium, tantalum, molybdenum, tungsten, vanadium or preferably chromium, calcium, magnesium, strontium and/or, more preferably barium, in excess of any present in the preformed support as impurities or cements.

By "promoting" is meant that the activity or preferably selectivity, is enhanced at any time in the life of the catalyst; the initial selectivity may for example thus be higher and/or it may be maintained for longer.

By "alkaline solution of the decomposable silver compound" is meant a solution which, when added to ten times its own volume of water, produces an alkaline reaction. The solution may comprise silver oxide or hydroxide or a silver salt, and a nitrogen-containing base which acts as a ligand, for example pyridine, acetonitrile, an amine especially a primary or secondary amine having 1 to 6 carbon atoms, or preferably ammonia; the silver dissolves in such solutions by complex formation. The solutions are suitably aqueous solutions and may contain 3 to 50% of silver by weight.

Impregnation may be carried out with a solution comprising 3 – 50% of silver by weight and a nitrogen containing ligand, for example acrylonitrile, ammonia and/or an amine, for example pyridine, hydroxylamine, an alkanolamine, for example ethanolamine, a vicinal alkylene diamine of from 2 – 4 carbon atoms (e.g. ethylene diamine) optionally together with a vicinal alkanolamine having 2 – 4 carbom atoms, or ammonia or ammonia and a vicinal alkanolamine. The ammonia and/or amine acts as a ligand.

The invention also provides catalysts for the production of alkylene oxides, for example ethylene and propylene oxides, by oxidation of the corresponding olefin with oxygen which comprise silver supported on and introduced by impregnation with an alkaline solution of a decomposable silver compound to a preformed porous heat resisting support, most of, preferably at least 80%, of the silver being present in the form of discrete particles adhering to the support having equivalent diameters of less than 10,000A, preferably in the range 200 to 10,000A, and more preferably 4,000 to 8,000A together with a promoting amount of copper, gold, magnesium, zinc, cadmium, mercury, strontium, calcium, niobium, tantalum, molybdenum, tungsten, chromium, vanadium, and/or preferably barium, in excess of any present in immobile form in the preformed support as impurities or cements.

This invention also provides a process for producing propylene oxide by contacting propylene and oxygen with a catalyst which comprises silver supported on and introduced by impregnation with a solution of a decomposable silver compound to a preformed porous heat reisting support, most of, preferably at least 80% of the silver being present in the form of discrete particles adhering to the support having equivalent diameters of less than 10,000A, preferably in the range 200 to 10,000A, together with a promoting amount of at least one promoter selected from lithium, potassium, sodium, rubidium, cesium, copper, gold, magnesium, zinc, cadmium, strontium, calcium, niobium, tantalum, molybdenum, tungsten, chromium, vanadium and barium, in excess of any present in immobile form in the preformed support as impurities or cements. The preferred promoter is barium. It is believed that the characteristics of the support affect the size of the silver particles.

In stating that "most of, preferably at least 80%, of the silver is present in the form of discrete particles adhering to the support and having equivalent diameters" in a given range, we judge the quantity of silver in terms of the number of particles falling in that range, though it may alternatively be judged in terms of the proportion of the surface area of the silver in that range. As assessment based on the mass of silver present in particles of a given size is less helpful since the existance of a few large particles of silver outside the range given may account for a large proportion of the silver by mass but have only a small effect on the catalyst.

By "equivalent diameter" is meant the diameter of a sphere of the same silver content as the particle. The particles of silver tend to adopt a rounded conformation, for example they may be hemispheres of somewhat greater actual diameter than the equivalent diameter. It is desirable for the silver particles to be as uniform in equivalent diameter as possible. The support in this form of the invention preferably has a specific surface area of below 10 $m^2/g$, and more preferably below 3 $m^2/g$, for example 0.1 to 1.5, especially 0.2 to 0.6 $m^2/g$; surface area being measured by the Brunauer, Emett and Teller method. The apparent porosity should be at least 20%, and is preferably 30 to 65%, more preferably 40 to 60%, for example 45 to 55%, as measured by the mercury absorption method, and median pore diameters should be 0.3 to 15, and preferably 1 to 15 microns, as measured by the mercury porosimetry method.

This invention also provides a process for producing ethylene oxide or propylene oxide, by contacting ethylene or propylene, and oxygen with a catalyst which comprises silver supported on and introduced by impregnation with a solution of a decomposable silver compound to a preformed porous heat resisting support, together with a. a promoting amount of sodium, cesium, rubidium, and/or potassium, and
b. magnesium, strontium, calcium and/or preferably barium in a promoting amount, the amount of components (a) and (b) being in excess of any present in immobile form in the preformed support as impurities or cements. Suitable supports may be as previously described.

The catalysts of this invention, or used in this invention, preferably comprise a promoting amount of an alkali metal, especially sodium, potassium or rubidium, and of an alkaline earth metal, for example strontium, calcium or, preferably, barium.

The silver may be present as silver or silver oxide. The dimensions of silver particles may be determined by scanning electron microscopy.

The support may be alumina, silicon carbide, silica, zirconia or silica/alumina support, but it is preferably composed of an aggregate of alpha-alumina particles which may be fused together or cemented together with, for example, silica or baryta.

The catalyst preferably comprises 3 to 15% and preferably 6 to 12% by weight of silver.

In general median pore diameters of 0.5 to 5 microns are preferred if the catalyst is in the form of small pellets of up to 6 mm., for example 0.4 to 6 mm. effective diameter and median pore diameters of 2 to 10 are preferred if the catalyst is in the form of larger pellets of over 2 mm., for example 2 to 8 mm. effective diameter. By "effective diameter" is meant the diameter of a sphere having the same volume to surface area ratio as the pellets. The pore size distribution may be bimodal (i.e. two groups of pores of distinctly different diameters may be present). In this cases one group accounting for a majority of the pores preferably has a median diameter in the range 0.3 to 15, and preferably 1 to 15 microns. Preferably at least half, and more preferably at least three quarters, of the pores have diameters in the range 0.3 to 15, and preferably 1 to 15 microns. The support preferably has a specific pore volume of 0.15 to 0.5, for example 0.15 to 0.35, and more preferably 0.17 to 0.3 cc/g. The ratio of median pore diameter to average equivalent diameter of the silver particles is suitably in the range 5 to 100, preferably 10 to 80, and more preferably 15 to 20.

Promoting amount of alkali metals ar generally smaller the greater the atomic weight of the alkali metal and are believed to increase with the concentration of any strontium, calcium and/or barium. In general 10 to 50,000, preferably 10 to 5,000 atoms of lithium, 1 to 30,000, preferably 1 to 5,000, more preferably 1 to 3,000, for example 10 to 3,000 or 50 to 1,000 atoms of sodium, 1 to 5,000, preferably 1 to 1,000, more preferably 10 to 500, and particularly 20 to 200 atoms of potassium, 0.01 to 500, preferably 0.01 to 100, more preferably 0.1 to 10, and particularly 1 to 8 atoms of rubidium, 0.01 to 500, preferably 0.01 to 100, more preferably 0.05 to 6, and particularly 0.5 to 5 atoms of cesium, are present per 1,000 atoms of silver. The amount of alkali metal used per 1,000 atoms of silver is generally higher the higher the olefine partial pressure, which may range for example, from 0.01 to 15 bars absolute.

Promoting amounts of copper, gold, magnesium, zinc, cadmium and/or mercury are preferably 1 to 500, and more preferably 1 to 100 atoms per 1,000 atoms of silver, and of calcium and/or barium are preferably 1 to 1,000, and more preferably 1 to 400, for example 1 to 200 or 1 to 100, atoms per 1,000 atoms of silver.

Promoting amounts of niobium, tantalum, molybdenum, tungsten, chromium and vanadium are preferably 0.001 to 10, preferably 0.01 to 5, and more preferably 0.1 to 2, atoms per 1,000 atoms of silver.

The invention also comprises a process for the production of a catalyst for the production of alkylene oxides by the oxidation of the corresponding olefins with oxygen which comprises impregnating a preformed porous heat resisting support with a solution of a silver compound which comprises a complexing and reducing component, and decomposing the silver compound, suitably by heating, in which process there is also introduced to the preformed support a promoting amount of copper, gold, magnesium, zinc, cadmium, strontium, mercury, calcium, niobium, tantalum, molybdenum, tungsten, chromium, vanadium and/or barium.

Impregnation may be carried out with a solution comprising 3 – 50% of silver by weight and a nitrogen-containing ligand, for example acrylonitrile, ammonia and/or an amine, for example pyridine, hydroxylamine, a vicinal alkylene diamine of from 2 – 4 carbon atoms (e.g. ethylene diamine) optionally together with vicinal alkanolamines having 2 – 4 carbon atoms, or ammonia or ammonia and vicinal alkanolamines. The ammonia and/or amine acts as a ligand. The reducing component may be an amine capable during heating of reducing the silver compound, or an anion of the silver compound, or may be an additional compound, for example formic acid, a $C_1$ to $C_6$ alcohol, a polyol, for example ethylene glycol, or a sugar or an aldehyde, for example formaldehyde. Suitable silver compounds include silver carboxylates, for example silver acetate, oxalate, citrate or lactate, silver carbonate and silver nitrate.

The promoters may be introduced with the silver as compounds soluble in the solution or by a separate impregnation step before or after introduction of the silver.

Suitably an aqueous solution of a compound of the promoter is used for impregnation. The nature of the compound is not critical, halides, for example chlorides, sulphates, nitrates, nitriles, carboxylates and many other compounds may be employed providing they are soluble in the solution. Compounds comprising two promoters, for example potassium dichromate, may be employed as may also complex compounds, especially ammines.

The alkali metal may be introduced by impregnating the preformed support preferably with an aqueous solution of an alkali metal compound which is preferably free from any inhibiting anions, for example a hydroxide, carbonate, bicarbonate, nitrate, nitrite, formate, acetate, oxalate, citrate or lactate. However, other compounds, for example the chlorides, may be used. Gold, cadmium and barium are very suitable promoters. Catalysts may comprise more than one of these elements especially barium, together with one of the others, for example barium/gold or barium/cadmium combinations. When co-deposited with silver, the soluble salts of these metals may be those capable of conversion to the oxide or metal under the conditions employed to reduce the silver compound to silver.

Thus, carboxylates, e.g. acetates, oxalates and lactates, nitrates and nitrites are preferred. Gold is suitably solubilised with a complexing agent, for example it can be impregnated as the thioxanate complex of gold (I) chloride.

It is desirable that silver should be deposited as discrete particles throughout substantially all of the available surface (inter alia within the pores) of the support as well as on the superficial surface. In order to ensure that as much of the silver and other element is in the pores of the support as possible rather than being deposited on the external surface of the support it is preferred that the total amount of solution used should be such that it is substantially entirely absorbed into the support rather than an excess being left in contact with it. Any surplus solution may alternatively be drained off prior to drying the solid. The silver compound may be decomposed by heating the impregnated support to a temperature of 200 – 400° C, preferably 200°– 350° C. Temperatures in the range 200° – 300° C are preferred when the decomposition is performed in the presence of a strong reducing agent, e.g. hydrogen or ethanolamine, but otherwise temperatures in the range 300° – 350° C are preferred for the decomposition of silver salts such as carboxylates, for example silver acetate, or combinations of silver salts with other metal carboxylates.

The conversion of ethylene to ethylene oxide using the catalysts of the invention may be carried out in a conventional manner. Pressures of from 1 to 35 bars absolute may be employed. The temperature is suitably in the range 190° to 270° C, preferably 210° to 245° C. In general a diluent, for example methane, is present in proportions of, for example 10 to 50% by weight. Generally 5 to 70, for example 50 to 70% of ethylene is converted and unconverted ethylene is recycled. Oxygen may be supplied, for example in the form of air or as commercial oxygen. Carbon dioxide is generally also present. A reaction modifier, for example ethylene dichloride, may be used to supress the formation of hot spots in the catalyst.

It is generally observed that in the production of propylene oxide conversion rate rises with total pressure of the reacting gases, but more particularly it rises as the partial pressure of oxygen is increased. Furthermore it is generally observed that the selectivity of the oxidation to propylene oxide rises as the ratio of oxygen pressure to propylene pressure is increased. It is preferred that the molar ratio of oxygen to propylene is in the range of about 0.05 to about 100, and more preferably in the range 0.1 to 5.

Partial pressures of propylene of 0.3 to 50 bars may be used. The total pressure may be in the range of from 1 – 100 bars absolute. The molar ratio of oxygen to propylene may be in the range 0.05 to 100. The partial pressure of oxygen may be in the range 0.02 to 10 bars, preferably 0.5 to 5 bars, and more preferably 1 to 4 bars, and may be supplied, for example in the form of air or as commercial oxygen. A diluent or a mixture of diluents, for example helium, nitrogen, argon, methane and carbon dioxide, may be present in molar proportions of up to 30 : 1, but preferably between 0.5 : 1 and 5 : 1 relative to the total number of moles of propylene and oxygen taken together. The temperature is suitably in the range 200° to 300° C, and preferably in the range 220° to 280° C. Contact times should be sufficient to convert 0.05 to 50%, for example 1 to 20% of propylene and unconverted propylene is recycled. Carbon dioxide may also be present. A reaction modifier, for example ethylene dichloride or vinyl chloride, may be used to improve catalyst performance and to minimise the formation of hot spots in the catalyst.

We have found that carbon dioxide may be used to raise the selectivity of the reaction. In this form of the process an olefine, especially propylene, and oxygen, are contacted with the catalyst in the presence of $CO_2$, the molar ration of $CO_2$ to $O_2$ being in the range 1 : 1 to 50 : 1, and preferably 2 : 1 to 10 : 1. Preferably the partial pressure of $CO_2$ is 0.5 to 50 bars, for example 1 to 10 bars, and more preferably 4 to 10 bars.

This invention also provides a process for producing propylene oxide by contacting propylene and oxygen with a catalyst which comprises silver supported on and introduced by impregnation with a solution of a decomposable silver compound to a preformed porous heatresisting support and a promoting amount of at least one promoter selected from lithium, potassium, sodium, rubidium, cesium, copper, gold, magnesium, zinc, niobium, tantalum, molybdenum, tungsten, chromium, vanadium, cadmium, strontium, calcium and barium, and preferably a promoting amount of potassium, sodium, rubidium and/or cesium together with a promoting amount of magnesium, strontium, calcium and/or preferably barium, the amounts being in excess of any present in immobile form in the preformed support as impurities or cements, in the presence of a concentration of one or more reaction modifiers which depresses the oxygen conversion in the process by 20 to 99%, preferably by 30 to 98%, and more preferably by 40 to 95% and which may be a component of the catalyst or may be fed in the gas phase during the reaction, which reaction modifier may comprise fluorine, chloride, bromine, iodine, bismuth, sulphur, selenium, tellurium and/or phosphorus. Catalysts in this form of the invention may be as disclosed previously.

It is preferred that the reaction modifier should comprise chlorine and it may be, for example, an alkyl chloride preferably having 1 to 6 carbon atoms, for example an methyl chloride or tert.butyl chloride; a chlorinated biphenyl or polyphenyl, dichlormethane or chloroform; a chlorinated benzene which may be, for example, monochloro or dichloro benzene; vinyl chloride or, preferably, ethylene dichloride. Corresponding bromine or iodine-containing compounds may be used, and sulphur, selenium, tellurium or phosphorus may be added as volatile organic compounds, oxides or hydrides. It is preferred that sulphur, selenium, tellurium or phosphorus should be added as a catalyst component as these elements are readily retained by the catalyst and maintain their effectiveness, whereas halogens are more readily removed from the catalyst and it is, therefore, preferred to feed them as before described in the gas phase, preferably continuously during the reaction.

When the reaction modifier comprises chlorine, it is preferred that it be added continuously at a level which provides by weight 5 to 10,000 and preferably 10 to 5,000 and more preferably 30 to 2,000, parts per million of chlorine based on the propylene. These proportions are in part dependent on reaction temperature, mole percent of propylene in the reaction mixture, flow rate of the gas mixture, pressure of the reaction and catalyst composition, but are also dependent in part on the nature of the reaction modifier; for example it is in general necessary to feed between about 2 – 12 times as much chlorine as vinyl chloride as is used with ethylene dichloride, between about 0.1 – 2 times as much when fed as monochlorobenzene and about 0.02 – 2 times as much when fed as dichlorobenzene.

Sulphur, selenium, tellurium and phosphorus may be supplied to the catalyst in the form of volatile organic compounds, for example mercaptans and phosphines, or volatile inorganic compounds, for example sulphur oxides and tellurium oxides, or they may be incorporated in the form of salts into the solid supported catalyst.

The catalysts in this form of the invention are preferably as hereinbefore described. The mean pore diameter of the support is, however, believed to be less critical and preferred mean pore diameters of the support are, therefore 1 to 100 microns, preferably 1 to 15 microns, and more preferably 2 to 10 microns as measured by the mercury porosimetry method. The support material is preferably alpha-alumina.

It has been found beneficial in some cases to regenerate the catalyst by exposure to oxidising conditions, for example by interrupting the feed of propylene. Propylene oxide is recovered from the product gases. Suitable techniques include solution extraction in water or an organic solvent, for example propylene glycol or a polyol, or condensate from the product gases may be used without purification in some cases in reactions, for example with acids or bases, etc. It is, of course, necessary to avoid operating under flammable or explosive conditions.

EXAMPLE 1

A catalyst (catalyst A) for the oxidation of ethylene to ethylene oxide was prepared as follows. 80 g. of reagent grade silver acetate was dissolved into 80 ml. aqueous ammonia (S.G. 0.880) and the solution was filtered. To the filtrate, which analysis showed contained 5.63 mole silver per litre, was added 12 ml. of ethanolamine. 60 ml. of this solution was added dropwise to 300 g. of support which was continuously stirred. The support was an alpha-alumina composite in the form of pellets which is sold by Norton Co. under the trademark ALUNDUM and which when crushed and sieved had diameters of 0.42 to 1 mm. The apparent porosity of the support was 40 to 44%. The water porosity of the support was 16 to 20%. This support impregnated with silver solution was heated in a forced draught oven for 4 hrs. whilst the temperature was raised from 100° C to 280° C at 0.8° C/min. This procedure resulted in a product containing 8% by weight of silver metal. (An alternative method of imbibing the silver solution into the support was to contact the support with excess silver solution followed by decantation or filtration).

EXAMPLE 2

A series of silver catalysts containing metal additives was prepared according to the procedure described in Example 1, except that a soluble salt of the metal additive was dissolved into the silver solution immediately prior to its impregnation in the support. Catalyst B contained 10 atoms cadmium added as Cd (OAc)$_2$ per 1,000 atoms Ag. Catalyst C contained 10 atoms of gold added as gold (I) chloride thioxanate per 1,000 atoms of silver, and Catalyst D contained 10 atoms of barium added as barium acetate per 1,000 atoms of silver. Catalyst G contained 10 atoms of zinc added as zinc acetate per 1,000 atoms of silver. Catalyst H contained 10 atoms of copper added as copper formate per 1,000 atoms of silver. Catalyst E contained 10 atoms of barium per 1,000 atoms Ag: it was prepared by impregnating the support used in Example 1 with aqueous barium hydroxide followed by heating at 300° C for 60 mins. in an atmosphere of $CO_2$ gas to convert the barium hydroxide to the carbonate. The support, now impregnated with barium, was loaded with silver as described in Example 1. Catalyst I contained 10 atoms of magnesium per 1,000 atoms of silver. It was prepared by the method described for catalyst E excepting that the support was impregnated with magnesium formate instead of barium hydroxide.

A silver catalyst (F) containing cadmium plus barium in the ratio of 10 atoms of cadmium and 130 atoms of barium per 1,000 atoms of silver was prepared as follows:

A support as used in Example 1 was impregnated with three quarters of the required barium as barium hydroxide which was converted to barium carbonate as for Catalyst E. All of the cadmium and one quarter of the barium was included in a silver solution as described for Catalysts B, C and D as cadmium and barium acetates.

EXAMPLE 3

Catalysts A to F were tested for catalyst activity in the following manner:

20 g. of catalyst was loaded into a glass reactor (internal diameter 8 mm.) contained in an air circulated thermostatically controlled oven. The catalyst was conditioned under increasingly severe reaction conditions until it reached a stable long term performance. A gas mixture containing 30% $C_2H_4$, 8% $O_2$, 62% $N_2$ and 4 p.p.m. ethylene dichloride was then passed over the catalyst at 1 bar pressure. The selectivity and conversion at 240° C and GHSV of 200h$^{-1}$ was determined. The gas velocity was varied to give conversions of 5% and 40% based on oxygen and the selectivity to ethylene oxide was determined. The results are displayed in the Table.

| Catalyst | Performance when GHSV = 200h$^{-1}$ | | C = 5 | C = 40 |
|---|---|---|---|---|
| | C | S | S | S |
| A | 24 | 79.5 | 81.5 | 78 |
| B | 23 | 83.8 | 85.9 | 82.0 |
| C | 3 | 89 | 90.2 | — |
| D | 21 | 86.0 | 86.7 | 85.2 |
| E | 20 | 88 | 88.7 | 86.8 |
| F | 25 | 87.6 | 90.1 | 85.9 |
| G | 60+ | 74 | 82+ | 78+ |
| H | 35 | 80 | 83 | 79 |
| I | 40 | 78 | 83 | 78 |

C = % oxygen conversion
S = yield of ethylene oxide (moles) per 100 moles of ethylene consumed
+ = at 230° C.

EXAMPLE 4

A catalyst for the oxidation of ethylene and propylene to ethylene oxide or propylene oxide, respectively was prepared as follows:

Sodium formate (0.175 g.) was dissolved in 11.85 ml. of a warm aqueous solution of barium hydroxide (12.6% w/w barium hydroxide). The resulting solution was impregnated into 30 g. of support. The support was an alpha-alumina composite in the form of pellets which is sold by Norton Co. under the trademark ALUNDUM and which when crushed and sieved had diameters of 0.42 to 1.0 mm. The apparent porosity of support was 50%; its porosity to water was 25%. The specific pore volume was 0.24 cc/g; surface area 0.36 m²/g. 95% of the pore volume was contained in pores with diameters in the range 1 – 15 microns. The mean pore diameter was 27 microns.

The impregnated support was heated in a forced air draught oven for 30 mins. at 300° C and then in an atmosphere of carbon dioxide for 60 mins. at 300° C.

The cooled impregnated support now comprising sodium and barium was impregnated with a second solution which this time was an aqueous solution containing 42% w/w of silver nitrate (9 ml.). This support impregnated with silver solution was dried at 110° C for 2 hours. The silver salt was reduced to silver metal by passing a stream of gas comprising 0.6% v/v hydrogen in nitrogen through a bed of the impregnated support for 6 hours and subsequently passing a stream of gas comprising 10% hydrogen in nitrogen for a further hour at a temperature of 220° C. This procedure resulted in a product containing 7.2% by weight of silver metal as determined by analysis.

EXAMPLE 5

The catalyst prepared in Example 4 (15 g.) was loaded into a glass reactor (internal diameter 8 mm.) contained in an air-circulated thermostatically controlled oven. The catalyst was used under increasingly severe reaction conditions until it reached a stable long term performance. A gas mixture containing ethylene (30%), nitrogen (62%), oxygen (8%) and ethylene dichloride (4 p.p.m.) was passed over the catalyst at 1 bar pressure. The selectivity at 240° C and GHSV of 200 h⁻¹ was determined. The gas velocity was varied to give conversions of 5% and 40% of the oxygen feedstock and the selectivity to ethylene oxide measured. The results are displayed in the Table.

| Performance when GHSV = 200h⁻¹ | | C = 5 | C = 40 |
|---|---|---|---|
| C | S | S | S |
| 2.8 | 89.0 | 88.8 | 85.0 |

EXAMPLE 6

The catalyst prepared in Example 4 (15 g.) was loaded into a glass reactor contained in a thermostatically controlled oven. A gas mixture containing propylene (30%), oxygen (8%), nitrogen (62%) and dichloromethane (500 p.p.m.) was passed over the catalyst at 1 bar pressure and a gas hourly space velocity (GHSV) of 200h⁻¹. At 240° C the selectivity to propylene oxide was 42% and the conversion of oxygen was 10%.

EXAMPLE 7

An alpha-alumina composite in the form of pellets sold by Norton Co. under the trademark ALUNDUM was crushed and sieved to give particles of diameters of 0.42 to 1 mm. The apparent porosity of the support was 40 to 44%, the water porosity of the support was 16 to 20%. The bulk density was 2.3 g/cc. and the apparent specific gravity was 3.95 g/cc; specific pore volume was 0.19 cc/g; surface area 0.17 m²/g, 100% of the pore volume was contained in pores in the range 1 to 40μ, 79% was in the range 1.5 to 15μ, and the mean pore diameter was 2.5μ.

Catalysts were made up to contain 8% by weight of silver and 130 atoms of barium per thousand atoms of silver, together (except in the case of catalyst J which is given as a blank for the purpose of comparison) with the specified amounts of alkali metal compound as follows:

The support was impregnated with three quarters of the required barium as barium hydroxide plus all of the alkali metal as the alkali metal formate. The barium and alkali metal were then converted to the carbonates by heating in an air atmosphere at 300° C for 30 minutes and then in an atmosphere of carbon dioxide at 300° C for 60 minutes. The remaining quarter of the barium was included as barium acetate in a silver solution prepared as follows:

80 g. of reagent grade silver acetate was dissolved in 80 ml. of aqueous ammonia (S.G. 0.880) and the solution was filtered. To the filtrate was added 12 ml. of ethanolamine. Barium acetate was added to the solution.

60 ml. of the solution was added dropwise to 300 grams of support which was continuously stirred. The support impregnated with the solution was heated in a forced draught oven for 4 hours whilst the temperature was raised from 100° C to 280° C at a rate of 0.8° C/minute.

The catalysts were tested for catalyst activity in the following manner:

20 grams of catalyst were loaded into a glass reactor of internal diameter 8 mm. contained in a thermostatically controlled circulated air oven. The catalyst was used under increasingly severe reaction conditions until it reached a stable long term performance. A gas mixture containing 30% ethylene, 8% oxygen, 62% nitrogen and 4 parts per million ethylene dichloride was then passed over the catalyst at 1 bar pressure. The selectivity and conversion at 240° C and a gas hourly spaced velocity of 200h⁻¹ was determined. The gas velocity was varied to give conversions of 5 and 40% based on oxygen and the selectivity of conversion of ethylene to ethylene oxide was determined. The results are displayed in the Table.

| Catalyst | Additive | Atoms of additive per 1000 atoms of Ag | Performance when GHSV = 200h⁻¹ | | C = 5 | C = 40 |
|---|---|---|---|---|---|---|
| | | | C | S | S | S |
| J | None | None | 13 | 80.5 | 82 | 78 |
| K | Rb | 10 | 13 | 87 | 88.5 | 81 |
| L | Cs | 4 | 11 | 87.5 | 89 | 81 |
| M | Cs | 2 | 22 | 87 | | |
| N | Na | 2 | 23 | 80.4 | 85.9 | 76.2 |
| O | Na | 10 | 16 | 87.5 | 91 | 80.0 |
| P | Na | 69 | 18 | 92.5 | 93.5 | 90.6 |
| Q | Na | 346 | 16 | 92 | 92.7 | 90.4 |
| R | Na | 692 | 9.2 | 90.8 | 91 | 90.1 |
| S | K | 10 | 21 | 89.5 | 92.5 | 86.0 |
| T | K | 70 | 19 | 87.5 | 88.6 | 85.8 |

C = % oxygen conversion.
S = yield of ethylene oxide (moles) per 100 moles of ethylene consumed.

On discharge after 40 hrs. the silver particles of Catalyst Q as determined by scanning electron microscopy were all in the range 0.1 to 1 micron equivalent diameter with more than 50% in the range 0.2 to 0.5 microns. Similar measurements for catalyst P showed that 100% were in the range 0.1 to 1.5 microns, 80% in the range 0.1 to 1.0 microns and 60% in the range 0.4 to 0.8 microns.

EXAMPLE 8

Silver catalysts 1 and 2 for the oxidation of ethylene to ethylene oxide were prepared as follows:

6 ml. of a freshly prepared solution, prepared by dissolving 8 g. reagent silver acetate in 8 ml. aqueous ammonia (S.G. 0.880), filtering and dissolving into the filtrate 1.2 ml. ethanolamine and 0.186 g. barium acetate, was added dropwise to 30 g. of a support which was continuously stirred. The support for catalyst 1 was an alpha-alumina composite in the form of pellets which is sold by Norton Co. under the trademark ALUNDUM and which when crushed and sieved had diameters of 0.42 to 1 mm. The apparent porosity of the support was 24.8%. The specific pore volume was 0.24 cc/g. and the specific surface area was 0.36 m$^2$/g. 95% of the pore volume was contained in pores with diameters in the range 1 to 15$\mu$ and 88% of the pore volume was contained in pores with diameters in the range 2 to 10$\mu$. The mean pore diameter was 2.7$\mu$. The support for catalyst 2 was an alpha-alumina composite in the form of pellets which is sold by Vereinigte Aluminium Werke Aktiengesellschaft (VAW) and which when crushed and sieved had diameters of 0.42 to 1 mm. The apparent porosity of the support was 40%. The water porosity of the support was 26%. The specific pore volume was 0.24 cc/g. and the specific surface area was 1.0 m$^2$/g. 95% of the pore volume was contained in pores with diameters in the range 0.1 to 3$\mu$ and 75% of the pore volume was contained in pores with diameters in the range 0.4 to 2.0$\mu$. The mean pore diameter was 0.8$\mu$. The support impregnated with the solution was heated in a fixed draught oven for 4 hrs. whilst the temperature was raised from 100° C to 300° C at 0.8° C/min.

EXAMPLE 9

Catalysts 1 and 2 were analysed and then tested for catalyst activity in the following manner.

20 g. of catalyst was loaded into a glass reactor (internal diameter 13 mm.) contained in an air circulated thermostatically controlled oven. A gas mixture containing 30% $C_2H_4$, 8% $O_2$, 62% $N_2$ and 4 p.p.m., ethylene dichloride was passed over the catalyst at 1 bar pressure and a gas hourly space velocity of 200h$^{-1}$. The selectivity to ethylene oxide (S), conversion of oxygen (C) and catalyst activity (A) were determined at 240° C. Catalyst compositions and results of activity tests are displayed in the Table.

S = Yield of olefine oxide (moles per 100 moles of olefin consumed),
C = % Oxygen conversion,
A = rate of olefin consumed (moles of olefine consumed per kilogram of catalyst per hour).

| Catalyst No. | Promoter Ba ppm | Catalyst Performance S % | C % | A m.Kg$^{-1}$h$^{-1}$ |
|---|---|---|---|---|
| 1 | 2000 | 86.9 | 11.6 | 0.19 |
| 2 | 2000 | 87.0 | 16.2 | 0.28 |

EXAMPLE 10

Silver catalysts 3 and 4 for the oxidation of ethylene oxide were prepared as follows:

6 ml. of a freshly prepared solution prepared by dissolving 8 g. silver acetate in 8 ml. aqueous ammonia (S.G. 0.880), filtering and dissolving into the filtrate 1.2 ml. ethanolamine, 0.186 g. barium acetate and 0.208 g. sodium acetate, was stirred with a support. The support for catalyst 3 was an alpha-alumina composite in the form of pellets which is sold by Norton Co. under the trademark ALUNDUM and which when crushed and sieved had diameters of 0.42 to 1 mm. The water porosity (which was equivalent to the mercury porosity) was 0.24 cc/g. or an apparent porosity of 40 − 44%, and the specific surface area was 0.36 m$^2$/g. 95% of the pore volume was contained in pores with diameters in the range 1 to 15$\mu$ and 88% of the pore volume was contained in pores with diameters in the range 2 to 10$\mu$. The mean pore diameter was 2.7$\mu$. The support for catalyst 4 was an alpha-alumina composite in the form of pellets which is sold by Vereiningte Aluminium-Werke Akteingesellschaft (VAW) and which when crushed and sieved had diameters of 0.42 to 1 mm. The apparent porosity of the support was 26%. The specific pore volume was 0.24 cc/g. and the specific surface area was 1.0 m$^2$/g. 95% of the pore volume was contained in pores with diameters in the range 0.1 to 3 and 75% of the pore volume was contained in pores with diameters in the range 0.4 to 20. The mean pore diameter was 0.8. The support impregnated with the solution was heated in a forced draught oven for 4 hrs. whilst the temperature was raised from 100° C to 300° C at 0.8° C/min. This procedure provides catalysts containing 8% by weight of silver.

EXAMPLE 11

Catalysts 3 and 4 were analysed and then tested for catalyst activity in the following manner.

20 g. of catalyst was loaded into a glass reactor (internal diameter 13 mm.) contained in an air circulated thermostatically controlled oven. A gas mixture containing 30% $C_2H_4$, 8% $O_2$, 62% $N_2$ and 4 p.p.m. ethylene dichloride was passed over the catalyst at 1 bar pressure and a gas hourly space velocity of 200h$^{-1}$. The selectivity to ethylene oxide (S), conversion of oxygen (C) and catalyst activity (A) were determined at 240° C. Catalyst compositions and results of activity tests are displayed in the Table:

S = Yield of olefin oxide (moles per 100 moles of olefin consumed),
C = % oxygen conversion,
A = rate of olefin consumed (moles of olefine consumed per kilogram of catalyst/hr.).

| Catalyst No. | Ba ppm | Na ppm | Catalyst Performance S % | C % | A m.kg$^{-1}$h$^{-1}$ |
|---|---|---|---|---|---|
| 3 | 2000 | 1180 | 89.8 | 24 | 0.15 |
| 4 | 2000 | 1180 | 90.8 | 32 | 0.29 |

EXAMPLE 12

The procedure of Example 7 was repeated using two catalysts with a high sodium to silver ratio. The barium to silver content was unchanged. Results were as follows:

| Atoms Na per 1000 atoms of Ag | Performance when GHSV = 200⁻¹ | | | |
|---|---|---|---|---|
| | C | S | C = 5 | C = 40 |
| 2,344 | 12.0 | 94.1 | 94.6 | 91.4 |
| 4,688 | 7.0 | 90.5 | 90.8 | 86.1 |

EXAMPLE 13

An alpha-alumina composite in the form of pellets sold by Norton Company under the trademark ALUNDUM was crushed and sieved to give particles of diameters of 0.42 to 1 mm. The apparent porosity of the support was 40 to 44%, the water porosity of the support was 16 to 20%.

A catalyst was made up to contain 8% by weight of silver and 130 atoms of barium and 2,344 atoms of sodium per thousand atoms of silver.

The support was impregnated with three quarters of the required barium as barium hydroxide plus all of the sodium as sodium formate. The barium and sodium were then converted to the carbonates by heating in an air atmosphere at 300° C for 30 minutes and then in an atmosphere of carbon dioxide at 300° C for 60 minutes. The remaining quarter of the barium was included as barium acetate in a silver solution prepared as follows.

80 g. of reagent grade silver acetate was dissolved in 80 ml. of aqueous ammonia (S.G. 0.880) and the solution was filtered. To the filtrate which contained 5.63 moles of silver acetate per litre was added 12 ml. of ethanolamine. Barium acetate was added to the solution.

The solution (about 60 mls.) was added dropwise to the support (300 g.) which was continuously stirred until the support appeared to have absorbed the solution to the limit of its porosity: the support then appeared wet and felt moist to the touch. The support impregnated with the solution was heated in a forced draught oven for 4 hrs. whilst the temperature was raised from 100° C at a rate of 0.8° C/minute.

The catalyst was tested for catalyst activity in the following manner.

20 grams of catalyst were loaded into a glass reactor of internal diameter 8 mm. contained in a thermostatically controlled circulated air oven. The catalyst was calcined under increasingly severe reaction conditions until it reached a stable long term performance. A gas mixture containing by volume 15% propylene, 4% oxygen and 81% nitrogen and 500 p.p.m. dichloromethane by weight, was then passed over the catalyst at 1 bar pressure. The selectivity and conversion at 240° C and a gas hourly space velocity of 200h⁻¹ was determined. The selectivity (i.e. yield of propylene oxide in moles per 100 moles of propylene consumed) was 48% and the oxygen conversion was 16%.

The above test was repeated except that the nitrogen in the gas mixture was replaced by $CO_2$. The selectivity was 55% and the oxygen conversion 10%.

EXAMPLE 14

Solutions containing silver and promoter/promoters was prepared by dissolving 8 g. reagent grade silver acetate in 8 mls. aqueous ammonia (S.G. 0,880), filtering and dissolving into the filtrate 1.2 mls. ethanolamine and promoter/promoters listed in the Table.

| Catalyst No. | Promoter/Promoters | |
|---|---|---|
| 5 | Barium acetate | 0.186 g. |
| 6 | Barium acetate | 0.186 g. |
| | Rubidium acetate | 0.085 g. |

6 ml. of the respective solution was impregnated into a support by adding it dropwise to the support (30 g.) which was continuously stirred. The support was an alpha-alumina composite in the form of pellets which is sold by Norton Co. under the trademark ALUNDUM and which when crushed and sieved had diameters of 0.42 to 1 mm. The apparent porosity of the support was 50%. The water porosity of the support was 24.8%. The specific pore volume was 0.24 cc/g. and the specific surface area was 0.36 m²/g. 95% of the pore volume was contained in pores with diameters in the range 1 – 15μ and 88% of the pore volume was contained in pores with diameters in the range 2 – 10μ. The mean pore diameter was 2.7μ.

The impregnated support was heated in a forced air draught oven for 4 hrs. whilst the temperature was raised from 100° C to 300° C at 0.8° C/min.

EXAMPLE 15

Catalyst 5 and 6 were analysed and then tested for catalyst activity in the following manner.

20 g. of catalyst was loaded into a glass reactor (internal diameter 13 mm.) contained in an air circulated thermostatically controlled oven. A gas mixture containing 30% $C_3H_6$, 8% $O_2$, 62% $N_2$ and 200 parts per million of ethylene dichloride based on the total gas feed was passed over the catalyst at 1 bar pressure and a gas hourly space velocity of 200h⁻¹. The selectivity to propylene oxide (S), conversion of oxygen (C) and catalyst activity (A) were determined at 240° C. Catalyst compositions and results of activity tests are displayed in the Table.

S = Yield of olefin oxide (moles per 100 moles of olefin consumed),

C = % oxygen conversion,

A = Rate of olefin consumed (moles of olefine consumed per kilogram of catalyst per hour).

| Catalyst No. | Composition | | Performance after 24 hrs. Oxidation of Propylene | | |
|---|---|---|---|---|---|
| | Ba ppm | Rb ppm | S % | C % | A m.kg⁻¹h⁻¹ |
| 5 | 2000 | nil | 35 | 15 | 0.04 |
| 6 | 2000 | 1000 | 48 | 11 | 0.025 |

EXAMPLE 16

A silver catalyst 7 for the oxidation of propylene to propylene oxide was prepared as follows.

6 ml. of a freshly prepared warm (30° C) solution D was added dropwise to 30 g. of support which was continuously stirred. The support was an alpha-alumina composite in the form of pellets which is sold by Norton Co. under the trademark ALUNDUM and which when crushed and sieved had diameters of 0.42 to 1 mm. The apparent porosity of the support was 50%. The water porosity of the support was 24.8%. The specific pore volume was 0.24 cc/g. and the specific surface area was 0.36 m²/g. 95% of the pore volume was contained in pores with diameters in the range 1 – 15 and 88% of the pore volume was contained in pores with diameters in the range 2 – 10 microns. The mean pore diameter was 2.7 microns. The impregnated support was first heated in an atmosphere of air at 300° C for 30 mins. and then in an atmosphere of $CO_2$ at 300° C for 60 mins. 6 ml. of freshly prepared solution E was then added dropwise to this treated support which was continuously stirred. The support impregnated with solution E was heated in a forced draught oven for 4 hrs. whilst the temperature was raised from 100° C to 300° C at 0.8° C/min. Solution E was prepared by dissolving 8 g. reagent grade silver acetate in 8 ml. aqueous ammonia (S.G. 0.880), filtering and dissolving into the filtrate 1.2 ml. ethanolamine and promoter/promoters as listed in the Table. Solution D was prepared by dissolving the appropriate weight of promoter/promoters in 10 ml. of warm water as listed in the Table.

| Catalyst No. | Promoter of solution E | Promoters of solution D |
|---|---|---|
| 7 | barium acetate : 0.33 g. | barium hydroxide : 1.26 g. sodium formate : 0.875g. |

EXAMPLE 17

Silver catalysts 8 and 9 for the oxidation of propylene to propylene oxide were prepared as follows.

6 ml. of freshly prepared solution F was added dropwise to 30 g. of support which was continuously stirred. The support was the same as that used in Example 16. This support impregnated with solution F was heated in a forced draught oven for 4 hrs. whilst the temperature was raised from 100° C to 300° C at 0.8° C/min. Solution F was prepared by dissolving 8 g. reagent grade silver acetate in 8 ml. aqueous ammonia (S.G. 0.880), filtering and dissolving into the filtrate 1.2 ml. ethanolamine and promoters as listed in the Table.

| Catalyst No. | Promoters |
|---|---|
| 8 | barium acetate : 0.186 g. sodium acetate : 1.05 g. |
| 9 | barium acetate : 0.186 g. sodium acetate : 1.78 g. |

EXAMPLE 18

Catalysts 7 and 9 were analysed and then tested for catalyst activity in the following manner.

20 g. of catalyst were loaded into a glass reactor (internal diameter 13 mm.) contained in an air circulated thermostatically controlled oven. A gas mixture containing 30% $C_3H_6$, 8% $O_2$, 62% $N_2$ and ethylene didichloride (EDC) was passed over the catalyst at 1 bar pressure and a gas hourly space velocity of $200h^{-1}$. The selectivity to propylene oxide (S), conversion of oxygen (C) and catalyst activity (A) were determined at 240° C. Catalyst compositions and results of activity tests are displayed in the Table. All the catalysts contained about 7 – 9% silver by weight.

S = Yield of olefin oxide (moles per 100 moles of olefin consumed
C = % oxygen conversion
A = Rate of olefin consumed (moles of olefine consumed per kilogram of catalyst per hour).

| Cat. No. | Ba ppm | Na ppm | EDC in Feed Gas | Performance after 24 hrs. Oxidation of Propylene | |
|---|---|---|---|---|---|
| | | | | S % | C % | A m.kg$^{-1}$h$^{-1}$ |
| 7 | 13,000 | 5,900 | 4 | 6 | 45 | 0.10 |
| 8 | 2,000 | 5,9000 | 12 | 10.5 | 40 | 0.07 |
| 9 | 2,000 | 10,000 | 200 | 40.6 | 19 | 0.04 |

EXAMPLE 19

Silver catalysts for the oxidation of propylene to propylene oxide were prepared as follows.

6 ml. of freshly prepared solution (I) was added dropwise to 30 g. of support which was continuously stirred. The support was an alpha-alumina composite in the form of pellets which is sold by Norton Co. under the trademark ALUNDUM and which when crushed and sieved had diameters of 0.42 to 1 mm. The apparent porosity of the support was 40 – 44%. The water porosity of the support was 16 – 20%. This support impregnated with solution (I) was heated in a forced draught oven for 4 hrs. whilst the temperature was raised from 100° to 300° C at 0.8° C/minute. Solution (I) was prepared by dissolving 8 g. reagent grade silver acetate in 8 ml. aqueous ammonia (S.G. 0.880), filtering and dissolving into the filtrate 1.2 ml. ethanolamine and a promoter as listed in the Table.

| Catalyst No. | Promoter | |
|---|---|---|
| 1' | none | |
| 2' | barium acetate | 0.0465 g. |
| 5' | sodium acetate | 0.175 g. |
| 7' | cadmium acetate $2H_2O$ | 0.103 g. |
| 8' | gold (I) thioxanate chloride | .112 g. |

EXAMPLE 20

Silver catalysts for the oxidation of propylene to propylene oxide were prepared as follows.

6 ml. of freshly prepared warm (30° C) solution II was added dropwise to 30 g. of support which was continuously stirred. The support was the same as that used in Example 19. The impregnated support was first heated in an atmosphere of air at 300° C for 30 mins. and and then in an atmosphere of $CO_2$ at 300° C for 60 mins. 6 ml. of freshly prepared solution (III) was then added dropwise to this treated support which was continuously stirred. The support impregnated with solution (III) was heated in a forced draught oven for 4 hrs. whilst the temperature was raised from 100° C to 300° C at 0.8° C/min. Solution (III) was prepared by dissolving 8 g. reagent grade silver acetate in 8 ml. aqueous ammonia (S.G. 0.880), filtering and dissolving into the filtrate 1.2 ml. ethanolamine and promoter/promoters as listed in the Table.

Solution (II) was prepared by dissolving the appropriate weight of promoter/promoters in 10 ml. of warm water as listed in the Table.

the trademark ALUNDUM and which when crushed and sieved had diameters of 0.42 to 1 mm. The apparent porosity of the support was 40 – 44%. The water porosity of the support was 16 – 20%. This support impregnated with solution was heated in a forced draught oven for 4 hrs. whilst the temperature was raised from 100° C to 300° C at 0.8° C/min. Solution (IV) was prepared by dissolving 8 reagent grade silver acetate in 8 ml. aqueous ammonia (S.G. 0.880), filtering and dissolving into the filtrate 1.2 ml. ethanolamine

| Catalyst No. | Promoter(s) of Solution (III) | | Promoter(s) of Solution (II) | | |
|---|---|---|---|---|---|
| 3' | none | | barium hydroxide 8H$_2$O | : | 1.26 g. |
| 4' | barium acetate | : 0.33 g. | barium hydroxide 8H$_2$O | : | 1.26 g. |
| 6' | none | | potassium formate | : | 0.0325 g. |
| 9' | barium acetate | : 0.33 g. | barium hydroxide 8H$_2$O | : | 1.26 g. |
|   |   |   | rubidium formate | : | 0.0077 g. |
| 10' | barium acetate | : 0.33 g. | barium hydroxide 8H$_2$O | : | 1.26 g. |
|   |   |   | rubidium formate | | 0.115 g. |
| 11' | barium acetate | : 0.33 g. | barium hydroxide 8H$_2$O | : | 1.26 g. |
|   |   |   | cesium formate | : | 0.0296 g. |
| 12' | barium acetate gold (I) thioxanate chloride | : 0.33 g. : 0.14 g. | barium hydroxide 8H$_2$O | : | 1.26 g. |

EXAMPLE 21

Catalysts 1' to 12' were analysed and then tested for catalyst activity in the following manner.

20 g. of catalyst was loaded into a glass reactor (internal diameter 13 mm.) contained in an air circulated thermostatically controlled oven. A gas mixture containing 30% $C_3H_6$, 8% $O_2$, 62% $N_2$ and 4 p.p.m. ethylene dichloride was passed over the catalyst at 1 bar pressure and a gas hourly space velocity of 200h$^{-1}$. The selectivity to propylene oxide (S), conversion of oxygen (C) and catalyst activity (A) was determined at 240° C. Catalyst compositions and results of activity tests are displayed in the Table.

S = Yield of olefin oxide (moles per 100 moles of olefin consumed)

C = % oxygen conversion

A = rate of olefin consumed (moles of olefine consumed per kilogram of catalyst per hour).

and barium acetate (.186 g.) and sodium acetate (.175 g.). The resulting catalyst is designated 13'.

EXAMPLE 23

Silver catalysts for the oxidation of propylene to propylene oxide were prepared as follows.

6 ml. of freshly prepared warm (30° C) solution (V) was added dropwise to 30 g. of support which was continuously stirred. The support was the same as that used in Example 22. The impregnated support was first heated in an atmosphere of air at 300° C for 30 mins. and then in an atmosphere of $CO_2$ at 300° C for 60 mins. 6 ml. of freshly prepared solution (VI) was then added dropwise to this treated support which was continuously stirred. The support impregnated with solution (VI) was heated in a forced draught oven for 4 hrs. whilst the temperature was raised from 100° C to 300° C at 0.8° C/min. Solution (VI) was prepared by dissolving 8 g. reagent grade silver acetate in 8 ml. aqueous

| Catalyst No. | Composition | | | | | | | Performance | | |
|---|---|---|---|---|---|---|---|---|---|---|
|  | Ba ppm | Na ppm | K ppm | Rb ppm | Cs ppm | Cd ppm | Au ppm | S % | C % | A m.kg$^{-1}$h$^{-1}$ |
| 1' | 500 | nil | nil | nil | nil | nil | nil | 11.7 | 36 | .069 |
| 2' | nil | nil | nil | nil | nil | nil | nil | 32 | 17 | .070 |
| 3' | 10,000 | nil | nil | nil | nil | nil | nil | 15.1 | 25 | .08 |
| 4' | 13,000 | nil | nil | nil | nil | nil | nil | 14.0 | 31.5 | .106 |
| 5' | nil | 1180 | nil | nil | nil | nil | nil | 38.3 | 22.2 | .123 |
| 6' | nil | nil | 300 | nil | nil | nil | nil | 51 | 6.6 | .025 |
| 7' | nil | nil | nil | nil | nil | 865 | nil | 19 | 25 | .070 |
| 8' | nil | nil | nil | nil | nil | nil | 1500 | 40 | 9.7 | .021 |
| 9' | 13,000 | nil | nil | 100 | nil | nil | nil | 26.9 | 6 | .029 |
| 10' | 13,000 | nil | nil | 1500 | nil | nil | nil | 59.9 | 7.6 | .049 |
| 11' | 13,000 | nil | nil | nil | 410 | nil | nil | 35 | 18.5 | .047 |
| 12' | 13,000 | nil | nil | nil | nil | nil | 1824 | 69.7 | 2.7 | .010 |

EXAMPLE 22

A silver catalyst for the oxidation of propylene to propylene oxide were prepared as follows.

6 ml. of freshly prepared solution (IV) was added dropwise to 30 g. of support which was continuously stirred. The support was an alpha-alumina composite in the form of pellets which is sold by Norton Co. under ammonia (S.G. 0.880), filtering and dissolving into the filtrate 1.2 ml. ethanolamine and promoter/promoters as listed in the Table.

Solution (V) was prepared by dissolving the appropriate weight of promoter/promoters in 10 ml. of warm water as listed in the Table.

The resulting catalysts are designated 14', 15', 16' and 17'.

| Catalyst No. | Promoters of solution (VI) | | | Promoters of Solution (V) | | |
|---|---|---|---|---|---|---|
| 14' | barium acetate | : | 0.33 g. | barium hydroxide 8H₂O sodium formate | : : | 1.26 g. .175 g. |
| 15' | barium acetate | : | 0.33 g. | barium hydroxide 8H₂O sodium formate | : : | 1.26 g. 1.75 g. |
| 16' | barium acetate | : | 0.33 g. | barium hydroxide 8H₂O potassium formate | : : | 1.26 g. 0.065 g. |
| 17' | barium acetate gold (I) thioxanate chloride | : : | 0.33 g. 0.14 g. | barium hydroxide 8H₂O sodium formate | : : | 1.26 g. 0.175 g. |

EXAMPLE 24

Catalysts 13' to 17' were analysed and then tested for catalyst activity in the following manner.

20 g. of catalyst was loaded into a glass reactor (internal diameter 13 mm.) contained in an air circulated thermostatically controlled oven. A gas mixture containing 30% $C_3H_6$, 8% $O_2$, 62% $N_2$ and 4 p.p.m. ethylene dichloride was passed over the catalyst at 1 bar pressure and a gas hourly space velocity of $200h^{-1}$. The selectivity to propylene oxide (S), conversion of oxygen (C) and catalyst activity (A) was determined at 240° C. Catalyst compositions and results of activity tests are displayed in the Table.

S = Yield of olefin oxide (moles per 100 moles of olefin consumed)
C = % oxygen conversion
A = rate of olefin consumed (moles of olefine consumed per kilogram of catalyst per hour).

| Catalyst No. | Composition | | | | Performance | | |
|---|---|---|---|---|---|---|---|
| | Ba ppm | Na ppm | K ppm | Au ppm | S % | C % | A m.kg⁻¹h⁻¹ |
| 13' | 2,000 | 1,180 | nil | nil | 36.2 | 15.0 | .09 |
| 14' | 13,000 | 1,180 | nil | nil | 42.1 | 19.3 | .107 |
| 15' | 13,000 | 11,800 | nil | nil | 44.3 | 19.9 | .019 |
| 16' | 13,000 | nil | 600 | nil | 61.6 | 4.8 | .019 |
| 17' | 13,000 | 1,180 | nil | 1824 | 61.6 | 2.2 | .007 |

Catalyst 14' was further contacted with a gas mixture containing 30% $C_3H_6$, 8% $O_2$, 62% $N_2$ and 1,000 p.p.m. dichloromethane at 1 bar pressure and a gas hourly space velocity of $200h^{-1}$. At 240° C the selectivity was 50%, conversion was 6% and the reaction rate was 0.02 $m.kg^{-1}h^{-1}$. In addition to providing high selectivity, a particular advantage was the stability of the catalyst performance.

EXAMPLE 25

The catalyst prepared in Example 1 (100 grams) was impregnated with a solution of chromium chloride, $CrCl_3$, $6H_2O$, (0.016 grams) dissolved in water (20 mls.). This was done by adding the aqueous solution dropwise to the continuously stirred catalyst. The chromium impregnated catalyst was heated in a forced draught oven for 4 hrs. whilst the temperature was raised from 100° C to 300° C at 0.8° C/min. This catalyst is designated 25A and contained 0.8 atoms of chromium per 1000 atoms of silver.

A similar catalyst was prepared by impregnating the support with the same level of chromium chloride (0.016 gram per 100 grams of gramsof support), drying the impregnated support by heating in a forced draught oven at 120° C for 1 hr. followed by impregnation with silver as described in Example 1. This catalyst is designated 25B.

EXAMPLE 26

The catalyst from Examples 1 and 25 were tested in the following manner.

20 g. of catalyst was loaded into a glass reactor (internal diameter 8 mm.) contained in an air circulated thermostatically controlled oven. The catalyst was conditioned under increasingly severe reaction conditions until it reached a stable long term performance. A gas mixture containing 30% $C_2H_4$, 8% $O_2$, 62% $N_2$ and 4 p.p.m. ethylene dichloride was then passed over the catalyst at 1 bar pressure. The selectivity and conversion at 240° C and GHSV of $200h^{-1}$ was determined. The gas velocity was varied to give conversions of 5% and 40% based on oxygen and the selectivity to ethylene oxide was determined. The results are displayed in the following Table.

| Catalyst | Performance when GHSv + 200h⁻¹ | | c = 5 | c = 40 |
|---|---|---|---|---|
| | C | S | S | S |
| From Example 1 | 24 | 80 | 82 | 78 |
| From Example 25A | 6 | 87 | 88 | 83 |
| From Example 25B | 7 | 88 | 88 | 84 |

The catalysts from Example 1 and 25 were also tested in the following manner.

20 g. of catalyst was loaded into a glass reactor (internal diameter 13 mm.) contained in an air circulated thermostatically controlled oven. A gas mixture containing 30% $C_3H_6$, 8% $O_2$, 62% $N_2$ and 500 p.p.m. dichloromethane was passed over the catalyst at 1 bar pressure and a gas hourly space velocity of $200h^{-1}$. The selectivity to propylene oxide (S), and conversion of oxygen (C) were determined at 240° C. Catalyst compositions and results of activity tests are displayed in the Table.

S = Yield of olefin oxide (moles per 100 moles of olefin consumed),
C = % oxygen conversion.

| Catalyst | Performance when GHSV = 200h$^{-1}$ | |
|---|---|---|
| | C | S |
| from Example 1 | 36 | 12 |
| from Example 25A | 20 | 40 |
| from Example 25B | 15 | 42 |

EXAMPLE 27

An alpha-alumina composite in the form of pellets sold by Norton Co. under the trademark ALUNDUM was crushed and sieved to give particles of diameters of 0.42 to 1 millimeter. The apparent porisity of the support was 40 to 44%, the water porosity of the support was 16 to 20%.

Catalysts 18', 19', 20' and 21' were made up to contain 8% by weight of silver and 130 atoms of barium per thousand atoms of silver, together (except in the case of catalyst 18' which is given as a blank for the purpose of comparison) with the specified amounts of alkali metal compound as follows.

The support was impregnated with three quarters of the required barium as barium hydroxide plus all of the alkali metal as the alkali metal formate. The barium and alkali metal were then converted to the carbonates by heating in an air atmosphere at 300° C for 30 mins. and then in an atmosphere of carbon dioxide at 300° C for 60 mins. The remaining quarter of the barium was included as barium acetate in a silver solution prepared as follows.

Reagent grade silver acetate (80 grms.) was dissolved in 80 ml. of aqueous ammonia (S.G. 0.880) and the solution filtered. An aqueous solution (12 ml.) of barium acetate was added to the filtrate.

Part of the solution (about 60 mls.) was added dropwise to 300 grams of support which was continuously stirred. The support impregnated with the solution was heated in a forced draught oven for 4 hrs. whilst the temperature was raised from 100° C to 300° C at a rate of 0.8° C/min.

The catalysts were analysed to contain about 8% Ag and tested for catalyst performance in the following manner.

20 grams of catalyst were loaded into a glass reactor of internal diameter 8 mm. contained in a thermostatically controlled circulated air oven. The catalyst was used under increasingly severe reaction conditions until it reached a stable long term performance. A gas mixture containing 30% ethylene, 8% oxygen, 62% nitrogen and 4 p.p.m. ethylene dichloride was then passed over the catalyst at 1 bar pressure. The selectivity and conversion at 240° C and a gas hourly space velocity of 200 h$^{-1}$ was determined. The gas velocity was varied to give conversions of 5 and 40% based on oxygen and the selectivity of conversion of ethylene to ethylene oxide was determined. The results are displayed in the Table.

In these Examples, GHSV means gas hourly space velocity.

In these Examples, other than in Example 4, the solutions used for impregnation with silver had an alkaline reaction when added to 10 times their own volume of water. Investigation of the catalysts of this invention by scanning electron microscopy indicates that most of the silver particles adhering to the support have equivalent diameters of less than 10,000A and more than 500A.

Porosity (i.e. specific pore volume), pore size distribution and median pore diameters of the supports in the invention are measured by mercury porosimetry as described by Ritter and Drake, Industrial and Engineering Chemistry, Analytical Edition, volume 17, pgs. 782 – 6, 1945.

We claim:

1. A catalyst for producing ethylene or propylene oxide by contacting ethylene or propylene and oxygen with the catalyst, which comprises
   a. silver supported on a preformed porous heat resisting support, in which said silver is introduced by impregnating said support with a solution of a decomposable silver compound and decomposing it to silver metal,
   b. a promoting amount of sodium, cesium, rubidium, potassium or mixtures thereof, and
   c. strontium, calcium, barium or mixtures thereof in a promoting amount, the amount of components (b) and (c) being in excess of any present in immobile form in the preformed support as impurities or cements.

2. A catalyst for the production of an alkylene oxide by oxidation of the corresponding olefin with oxygen, which comprises silver supported on a preformed porous heat resisting support in which said silver is introduced by impregnating said support with a solution of a decomposable silver compound in which said solution is alkaline or said solution contains a nitrogen - containing base complexing agent and a reducing component and said silver compound is decomposed to silver metal, said catalyst being characterized as:
   i. having a specific surface area in the range 0.04 to 10 m$^2$/g. as measured by the Brunauer, Emmett and Teller method, an apparent porosity as measured by the mercury absorption method of at least 20%, and median pore diameters of 0.3 to 15 microns, as measured by the mercury porosimetry method;

said catalyst further comprising
   a. promoting amount in excess of any present in said preformed support of at least one member selected from the group consisting of copper, gold, zinc, cadmium, mercury, niobium, tantalum, molybdenum, tungsten, vanadium, chromium, calcium, magnesium, strontium and barium, and
   b. a promoting amount of at least one of the group consisting of sodium, potassium, cesium and rubidium.

| Catalyst | Additive | Atoms of additive per 1000 atoms of Ag | performance when GHSV = 200$^{-1}$ | | C = 5 | C = 40 |
|---|---|---|---|---|---|---|
| | | | C | S | S | S |
| 18' | None | None | 11.3 | 83.6 | 84.0 | 72.9 |
| 29' | Na | 69 | 15 | 88.6 | 89.6 | 85.4 |
| 20' | Na | 692 | 10 | 90.6 | 90.9 | 87.1 |
| 21' | K | 70 | 14 | 88.1 | 89.7 | 85.2 |

C = % oxygen conversion.
S = Yield of ethylene oxide (moles per 100 moles of ethylene consumed.

3. A catalyst as claimed in claim 2 in which the complexing agent provides the reducing component.

4. A catalyst as claimed in claim 3 in which the complexing agent providing the reducing component is an amine capable during heating of reducing the silver compound.

5. A catalyst as claimed in claim 2 in which the promotors comprise barium and sodium or potassium.

6. A catalyst as claimed in claim 2 in which most of the silver particles are discrete particles adhering to said support having equivalent diameters of less than 10,000 A.

* * * * *

UNITED STATES PATENT OFFICE
CERTIFICATE OF CORRECTION

Patent No. 4,007,135  Dated February 8, 1977

Inventor(s) Percy Hayden; Roy John Sampson; Christopher Buxton Spencer; and Harry Pinnegar It is certified that error appears in the above-identified patent and that said Letters Patent are hereby corrected as shown below:

IN THE HEADING:

At section [30] relating to Foreign Application Priority Data, please correct the first five filing dates to read:

-- December 5, 1973
   January 9, 1974
   January 9, 1974
   April 3, 1974
   April 3, 1974 --.

Signed and Sealed this

Thirteenth Day of September 1977

[SEAL]

Attest:

RUTH C. MASON
Attesting Officer

LUTRELLE F. PARKER
Acting Commissioner of Patents and Trademarks